United States Patent
Hong et al.

(10) Patent No.: US 9,968,440 B2
(45) Date of Patent: May 15, 2018

(54) OPHTHALMIC LENS HAVING AN EXTENDED DEPTH OF FOCUS

(71) Applicant: NOVARTIS AG, Basel (CH)

(72) Inventors: Xin Hong, Fort Worth, TX (US); Zoran Milanovic, Fort Worth, TX (US); Xin Wei, Frisco, TX (US)

(73) Assignee: Novartis AG, Basel (CH)

(*) Notice: Subject to any disclaimer, the term of this patent is extended or adjusted under 35 U.S.C. 154(b) by 0 days. days.

(21) Appl. No.: 15/055,993

(22) Filed: Feb. 29, 2016

(65) Prior Publication Data
US 2017/0245983 A1    Aug. 31, 2017

(51) Int. Cl.
| | | |
|---|---|---|
| *A61F 2/16* | (2006.01) | |
| *G02B 27/00* | (2006.01) | |
| *G02C 7/04* | (2006.01) | |
| *G02C 7/06* | (2006.01) | |

(52) U.S. Cl.
CPC ............ *A61F 2/1618* (2013.01); *A61F 2/164* (2015.04); *A61F 2/1613* (2013.01); *A61F 2/1616* (2013.01); *A61F 2002/1683* (2013.01); *G02B 27/0075* (2013.01); *G02C 7/044* (2013.01); *G02C 7/06* (2013.01)

(58) Field of Classification Search
CPC .... A61F 2/1613; A61F 2/1616; A61F 2/1637; A61F 2/164; A61F 2/1654; A61F 2/1618; G02C 7/044; G02C 7/06
See application file for complete search history.

(56) References Cited

U.S. PATENT DOCUMENTS

| | | | |
|---|---|---|---|
| 6,536,898 B1 | 3/2003 | Cathey, Jr. | |
| 6,830,332 B2 * | 12/2004 | Piers .................... | G02B 5/1895 351/159.11 |
| 7,025,454 B2 | 4/2006 | Cathey, Jr. | |
| 7,061,693 B2 | 6/2006 | Zalevsky | |
| 7,073,906 B1 | 7/2006 | Portney | |
| 7,365,917 B2 | 4/2008 | Zalevsky | |
| 7,859,769 B2 | 12/2010 | Zalevsky | |
| 8,192,022 B2 | 6/2012 | Zalevsky | |
| 8,430,508 B2 | 4/2013 | Weeber | |
| 8,926,092 B2 | 1/2015 | Weeber | |
| 9,216,080 B2 | 12/2015 | Bogaert et al. | |
| 9,329,407 B2 | 5/2016 | Cathey, Jr. et al. | |
| 2006/0034003 A1 | 2/2006 | Zalevsky | |
| 2010/0161051 A1 | 6/2010 | Hong | |

OTHER PUBLICATIONS

Weeber, H.A. et al., "Extending the range of vision using diffractive intraocular lens technology," J Cataract Refract Surg Jul. 2015; 41:2746-2754, 2015 ASCRS and ESCRS, 9 pgs.

* cited by examiner

*Primary Examiner* — Howie Matthews

(57) ABSTRACT

In certain embodiments, an ophthalmic lens includes an optic having an anterior surface, a posterior surface, and an optical axis. At least one of the anterior surface and the posterior surface includes a first zone extending from the optical axis to a first radial boundary and a second zone extending from the first radial boundary to the edge of the optic. The first zone includes an inner region and an outer region separated by a phase shift feature, the phase shift comprising a ridge extending outwardly from the inner region and the outer region.

8 Claims, 6 Drawing Sheets

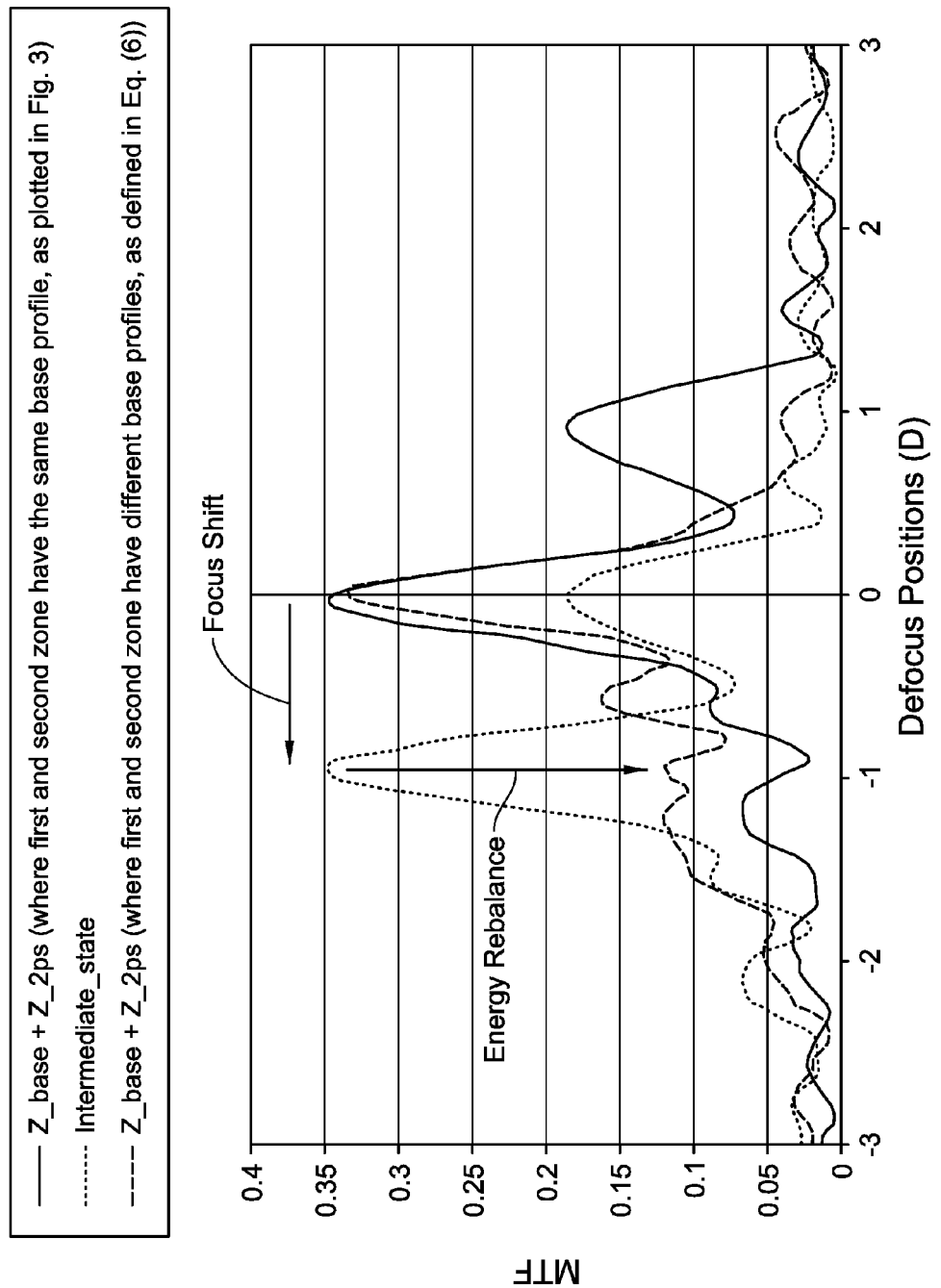

OPHTHALMIC LENS HAVING AN EXTENDED DEPTH OF FOCUS

FIELD

This present disclosure relates generally ophthalmic lenses and, more particularly, to ophthalmic lenses having an extended depth of focus.

BACKGROUND

Intraocular lenses (IOLs) are routinely implanted in patients' eyes during cataract surgery to replace the natural crystalline lens. The optical power of the natural crystalline lens can vary under the influence of the ciliary muscles to provide accommodation for viewing objects at different distances from the eye. Many IOLs, however, provide a monofocal power with no provision for accommodation. Multifocal IOLs are also known that provide a distance optical power as well as a near optical power (e.g., by employing diffractive structures), thereby providing a degree of pseudoaccommodation. There is, however, still a need for improved IOLs that can provide pseudo-accommodative optical power.

SUMMARY

The present disclosure generally concerns ophthalmic lenses (e.g., IOLs) that provide (1) controlled variation of multiple phase shifts within the pupil region to extend the depth-of-focus and (2) power adjustment in the central sub-area of the pupil region to shift the through-focus curve and to rebalance the energy between intermediate correction and the distance correction. In certain embodiments, an ophthalmic lens includes an optic having an anterior surface, a posterior surface, and an optical axis. At least one of the anterior surface and the posterior surface includes a first zone extending from the optical axis to a first radial boundary and a second zone extending from the first radial boundary to the edge of the optic. The first zone includes an inner region and an outer region separated by a phase shift feature, the phase shift comprising a ridge extending outwardly from the inner region and the outer region.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein:

FIG. 5 illustrates a through focus plot for the optic surface profile depicted in FIG. 4 as compared to the through focus plot for the optic depicted in FIG. 2, according to certain embodiments of the present disclosure.

The skilled person in the art will understand that the drawings, described below, are for illustration purposes only. The drawings are not intended to limit the scope of the applicant's disclosure in any way.

DETAILED DESCRIPTION

The present disclosure is generally directed to an ophthalmic lens (such as an IOL) having a surface profile that produces a controlled variation of phase shifts in light waves passing through various regions of the lens in a manner that extends the depth-of-focus. In the following description, the lens features providing an extended depth of focus are described in connection with intraocular lenses (IOLs). However, the present disclosure contemplates that those features can also be applied to other ophthalmic lenses, such as contact lenses. As used herein, the term intraocular lens (and its abbreviation IOL) are used to describe lenses that are implanted into the interior of the eye to either replace the eye's natural lens or to otherwise augment vision regardless of whether or not the natural lens is removed.

Figure 1A:
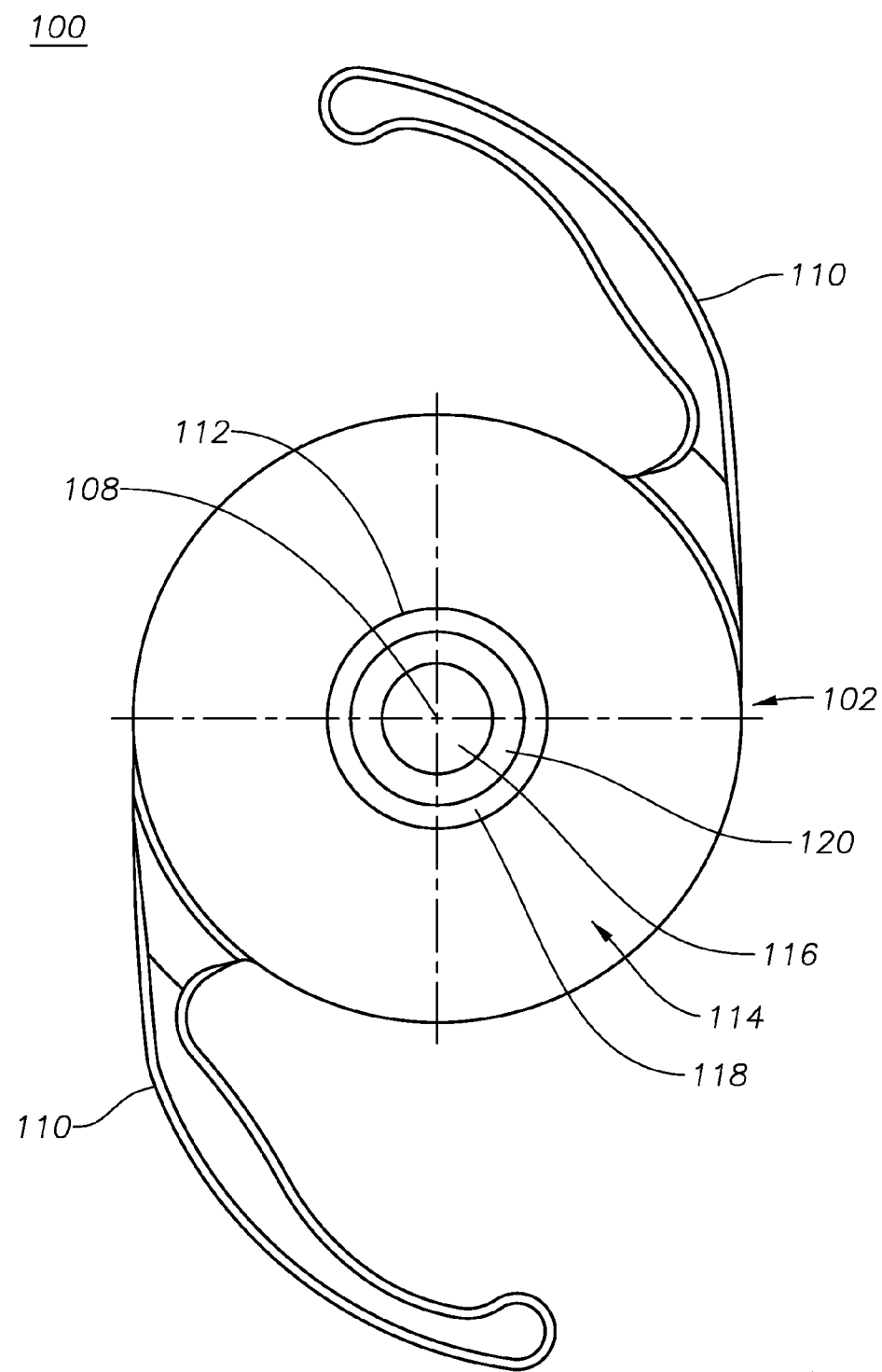
FIGS. 1A-1B illustrate and example embodiment of an intraocular lens having an extended depth of focus, according to certain embodiments of the present disclosure.
Figure 1B:
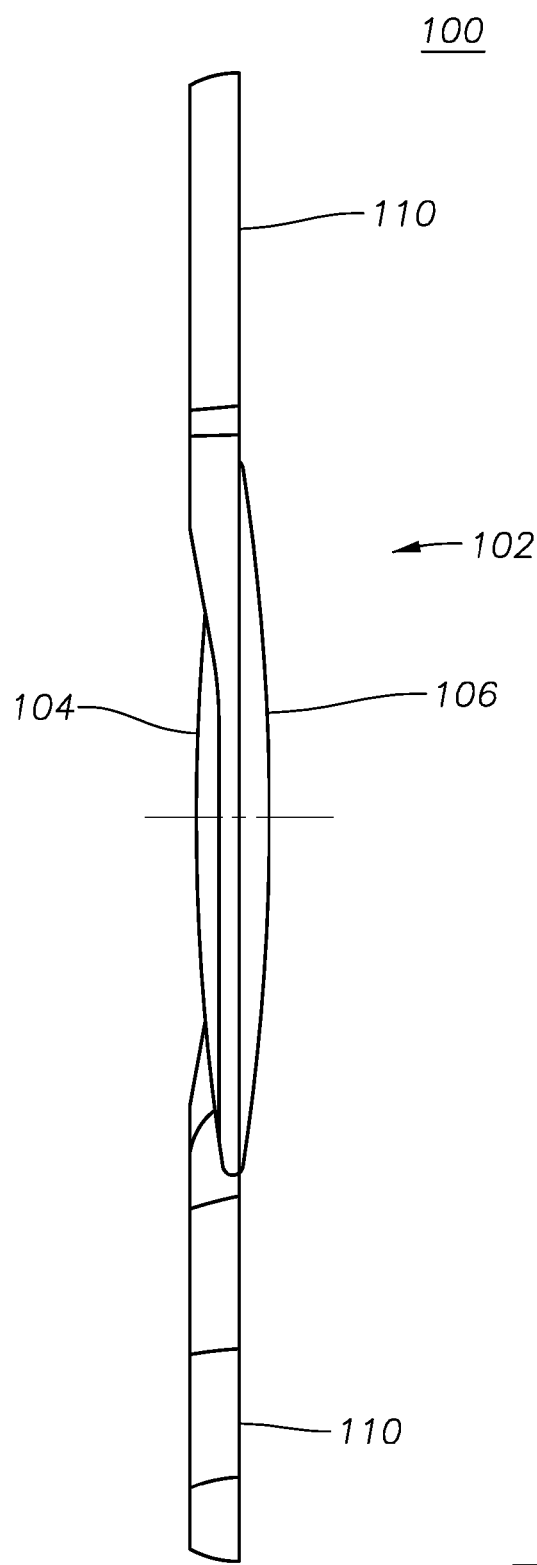

FIGS. 1A-1B illustrate and example embodiment of an intraocular lens 100 having an extended depth of focus, according to certain embodiments of the present disclosure. IOL 100 includes an optic 102 having an anterior surface 104 and a posterior surface 106 that are disposed about an optical axis OA 108. IOL 100 may further include a plurality of haptics 110 generally operable to position and stabilize IOL 100 within the capsular bag of a patient's eye.

As shown in FIG. 1A, the anterior surface 104 of optic 102 includes a first zone 112 extending from the optical axis 108 to a first radial boundary and a second zone 114 extending from the first radial boundary to the edge of the optic 102. Additionally, the first zone 112 may include an inner region 116 and an outer region 118 separated by a phase shift feature 120. In general, the above-described surface features of optic 102 may produce varying amount of phase shift of light waves passing through optic 102 (depending upon the region of the optic 102 the light waves pass through), and constructive interference between the light waves having varying amounts of phase shift may produce an extended depth of focus. Although the above-described first and second zones 112, 114 are depicted and described as being located on anterior surface 104 of optic 102, the present disclosure contemplates that first and second zones 112, 114 may additionally or alternatively be located on posterior surface 106 of optic 102.

In certain embodiments, phase shift feature 120 may include a ridge projecting anteriorly from the anterior surface 104 of optic 102. As a result, moving radially outward from the optical axis 108, phase shift feature 120 may result in two phase shift steps. For example, the surface profile of the first zone may be defined by the following equation:

$$Z_{first\ zone} = Z_{base} + Z_{2ps} \quad \text{Eq. (1)}$$

In Eq. (1), $Z_{base}$ may define a base sag profile for the first zone according to the following equation:

$$Z_{base} = \frac{cr^2}{1 + \sqrt{1 - (1+k)c^2 r^2}} + a_2 r^2 + a_4 r^4 + a_6 r^6 + \ldots + a_n r^n \quad \text{Eq. (2)}$$

wherein, r is a radial distance from the optical axis 108;

c is a base curvature of the first zone 112;

k is a conic constant; and $a_2, a_4, a_6, \ldots,$ and $a_n$ are, respectively, second, fourth, sixth, . . . , and $n^{th}$ order coefficients.

In certain embodiments, the equation defining $Z_{base}$ may only include second, fourth, and sixth order coefficients. In other words, $Z_{base}$ may define a base sag profile for the first zone according to the following equation:

$$Z_{base} = \frac{cr^2}{1 + \sqrt{1 - (1+k)c^2r^2}} + a_2r^2 + a_4r^4 + a_6r^6 \quad \text{Eq. (3)}$$

Although Eq. (2) and Eq. (3) generally define aspheric surface profiles, the present disclosure contemplates that the constants includes in those equations may be selected such that they define a spheric profile. In other words, the base curvature of the first zone ($Z_{base}$) may be either spheric or aspheric.

In Eq. (1), $Z_{2ps}$ may be added to the base sag profile ($Z_{base}$) and may, in part, define the features of the phase shift region 120. For example, $Z_{2ps}$ may be defined by the following equation:

$$Z_{2ps} = \begin{cases} 0 & r_0 \leq r < r_1 \\ (r-r_1)/(r_2-r_1)*\Delta_1 & r_1 \leq r < r_2 \\ \Delta_1 & r_2 \leq r < r_3 \\ \Delta_1 + (r-r_3)/(r_4-r_3)*\Delta_2 & r_3 \leq r < r_4 \\ \Delta_1 + \Delta_2 & r_4 \leq r < r_5 \end{cases} \quad \text{Eq. (4)}$$

where, r is a radial distance from the optical axis 108;

$r_0$ is the optical axis 108;

the inner region 116 extends from the optical axis 108 to $r_1$ the phase shift feature 120 extends from $r_1$ to $r_4$;

the outer region 118 extends from $r_4$ to $r_5$;

$\Delta_1$ is a step height of the phase shift 120 feature relative to the inner region 116; and $\Delta_2$ is a step height of the phase shift feature relative to the outer region 118.

Figure 2:
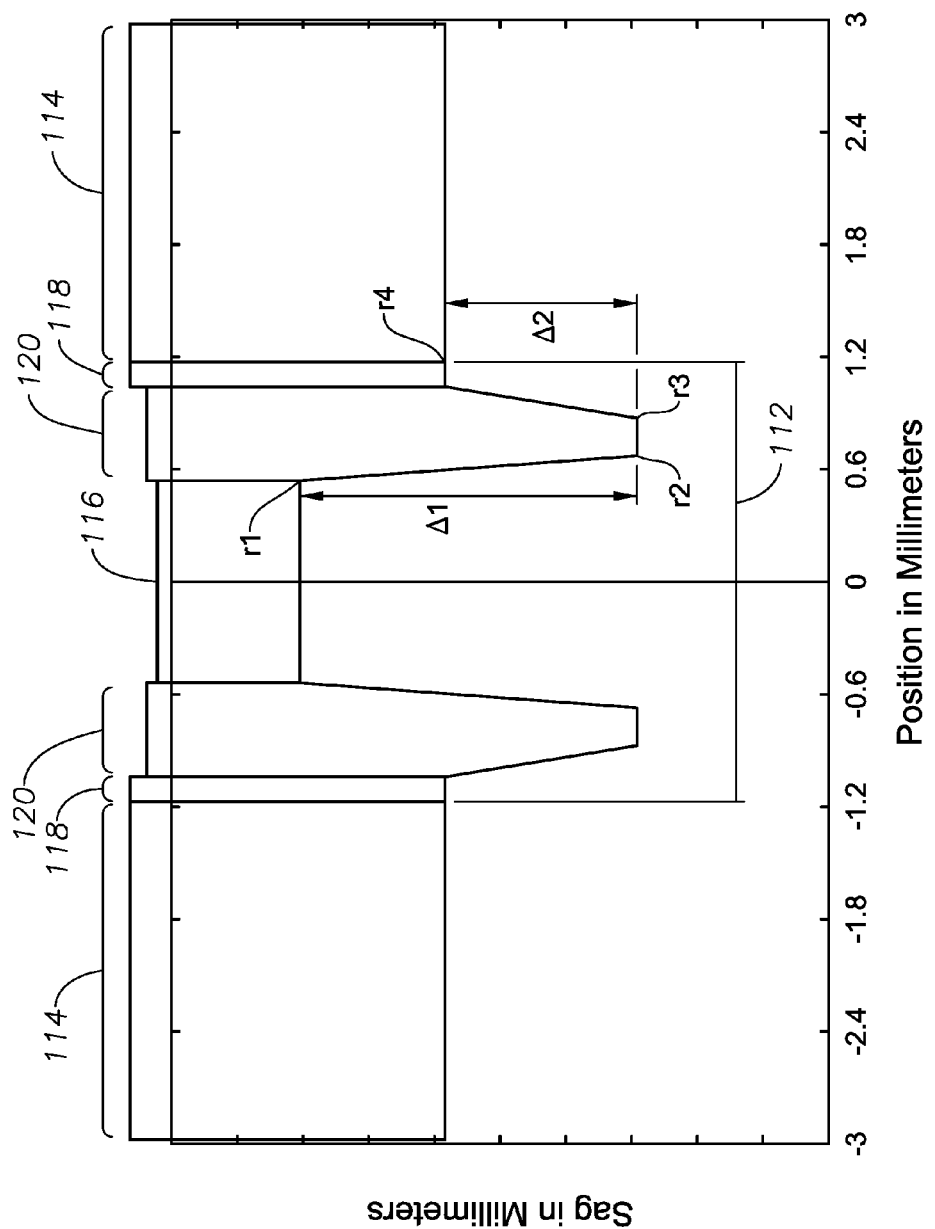
FIG. 2 illustrates an plot of surface sag versus radial distance from the optical axis for an exemplary optic having inner and outer zones with the same base curvature, according to certain embodiments of the present disclosure.

The overall surface profile of optic 102, as defined by Eqs. (1)-(4), may be graphically represented as a plot of sag vs. radial distance from the optical axis 108, as shown in FIG. 2. In the plot of FIG. 2, the sag values have been normalized by removing the contribution of $Z_{base}$ (i.e., the plotted sag value corresponds only to $Z_{2ps}$). Additionally, in the plot of FIG. 2, the sag profile is constant for the first zone 112 and the second zone 114. In other words, it is assumed that Eq. (1) defines the surface profile of the entire optic 102 as opposed to only the first zone 112 (meaning that, in Eq. (4), $r_5$ corresponds to the radius of the entire optic 102).

Figure 3:
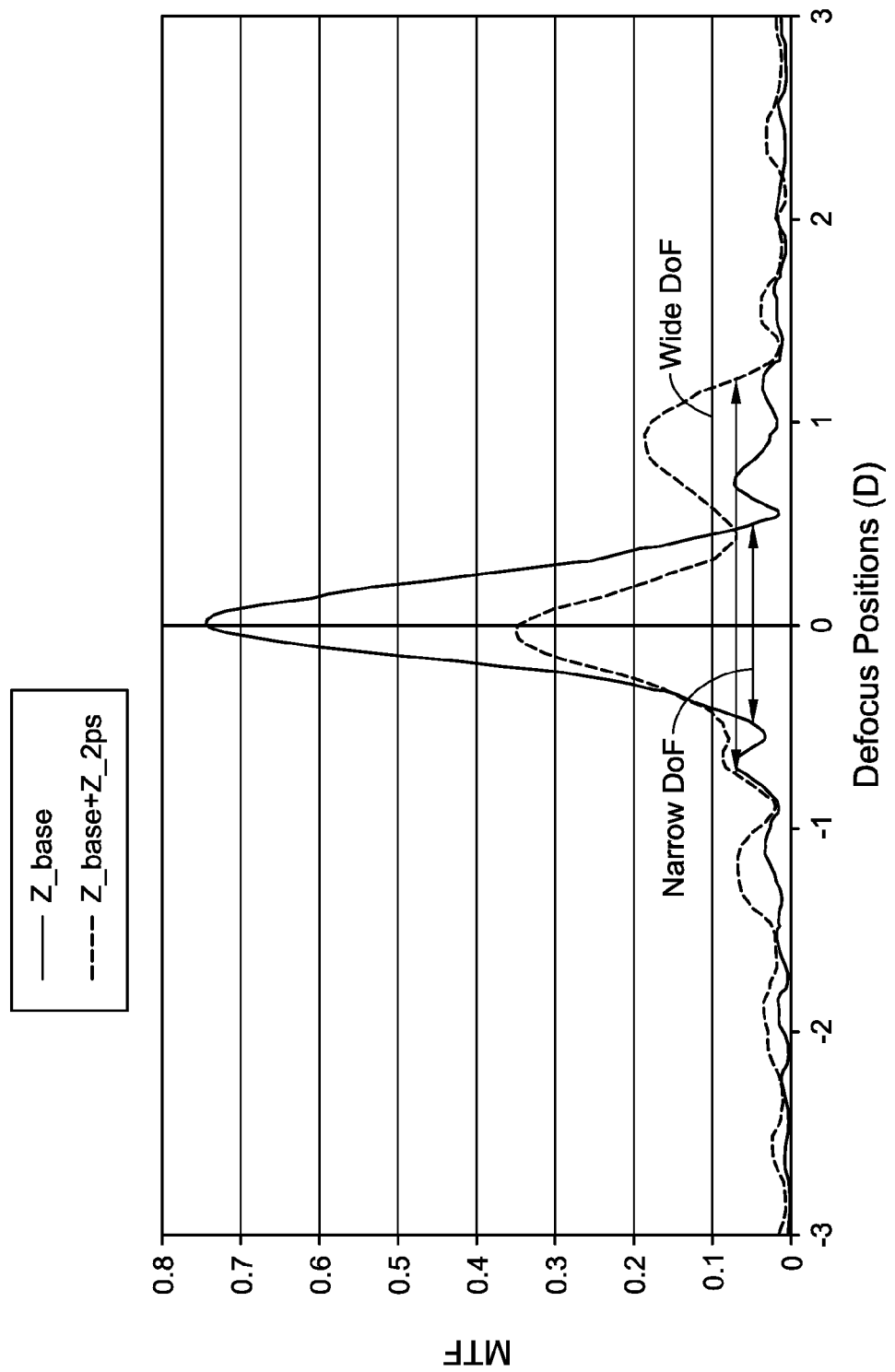
FIG. 3 illustrates a through focus plot for the optic surface profile depicted in FIG. 2 as compared to the through focus plot for a standard aspheric optic, according to certain embodiments of the present disclosure.

FIG. 3 illustrates a through focus plot for the optic surface profile depicted in FIG. 2 as compared to the through focus plot for a standard aspheric optic (i.e., an optic having a surface profile defined only by Eq. (3) ($Z_{base}$) without the addition of Eq. (4) ($Z_{2ps}$)), according to certain embodiments of the present disclosure. As is illustrated, the addition of the surface profile depicted in FIG. 2 (including the phase shift feature 120 represented by $Z_{2ps}$) results in a wider depth of focus as compared to a standard aspheric lens.

In certain embodiments, the base sag profile may be different for the first zone 112 and the second zone 114. For example, the surface profile of the optic 102 may be defined by the following equation:

$$Z_{optic} = Z_{base} + Z_{2ps} \text{ where,} \quad \text{Eq. (5)}$$

$$Z_{base} = \begin{cases} \frac{cr^2}{1 + \sqrt{1-(1+k)c^2r^2}} + a_2r^2 + a_4r^4 + a_6r^6 & r_0 \leq r < r_5 \\ \frac{c'r^2}{1 + \sqrt{1-(1+k')c'^2r^2}} + a_2'r^2 + a_4'r^4 + a_6'r^6 & r_5 \leq r < r_6 \end{cases} \quad \text{Eq. (6)}$$

$$Z_{2ps} = \begin{cases} 0 & 0 \leq r < r_1 \\ (r-r_1)/(r_2-r_1)*\Delta_1 & r_1 \leq r < r_2 \\ \Delta_1 & r_2 \leq r < r_3 \\ \Delta_1 + (r-r_3)/(r_4-r_3)*\Delta_2 & r_3 \leq r < r_4 \\ \Delta_1 + \Delta_2 & r_4 \leq r < r_5 \\ \Delta_3 & r_5 \leq r < r_6 \end{cases} \quad \text{Eq. (7)}$$

$$\Delta_3 = \left[\frac{(cr_5^2)}{\left(1+\sqrt{(1-(1+k)c^2r_5^2)}\right)} + a_4r_5^4 + a_6r_5^6 + \Delta_1 + \Delta_2\right] - \left[\frac{(c'r_5^2)}{\left(1+\sqrt{(1-(1+k')c'^2r_5^2)}\right)} + a_4'r_5^4 + a_6'r_5^6\right] \quad \text{Eq. (8)}$$

r is a radial distance from the optical axis 108;

$r_0$ is the optical axis 108;

the first zone 112 extends from optical axis 108 to $r_5$, with the inner region 116 extending from the optical axis 108 to $r_1$, the phase shift feature 120 extending from $r_1$ to $r_4$, and the outer region 118 extending from $r_4$ to $r_5$;

the second zone 114 extends from $r_5$ to $r_6$;

c is a base curvature of the first zone 112;

k is a conic constant of the first zone 112; and $a_2, a_4,$ and $a_6$ are, respectively, second, fourth, and sixth order coefficients of the first zone 112;

c' is a base curvature of the second zone 114;

k' is a conic constant of the second zone 114; and $a_2', a_4',$ and $a_6'$ are, respectively, second, fourth, and sixth order coefficients of the second zone 114;

$\Delta_1$ is a step height of the phase shift feature 120 relative to the inner region 116; and $\Delta_2$ is a step height of the phase shift feature 120 relative to the outer region 118.

Although base profiles defined in Eq. (6) above only include second, fourth, and sixth order coefficients, the present disclosure contemplates that those base profiles could alternatively be defined as including any suitable number of higher order coefficients (as in Eq. (1)).

Figure 4:
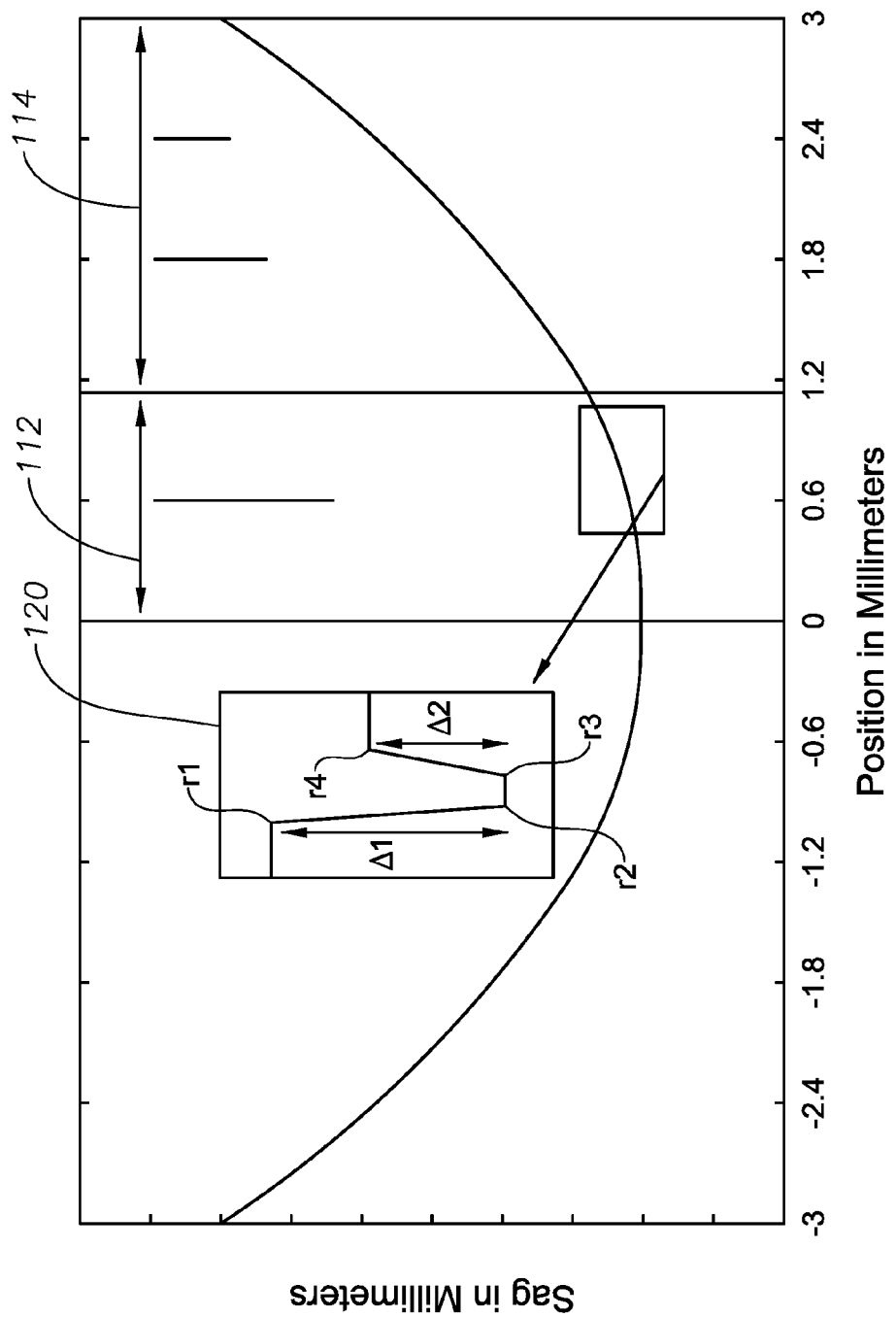
FIG. 4 illustrates a plot of surface sag versus radial distance from the optical axis for an exemplary optic having inner and outer zones with different base curvatures, according to certain embodiments of the present disclosure.
Figure 2:
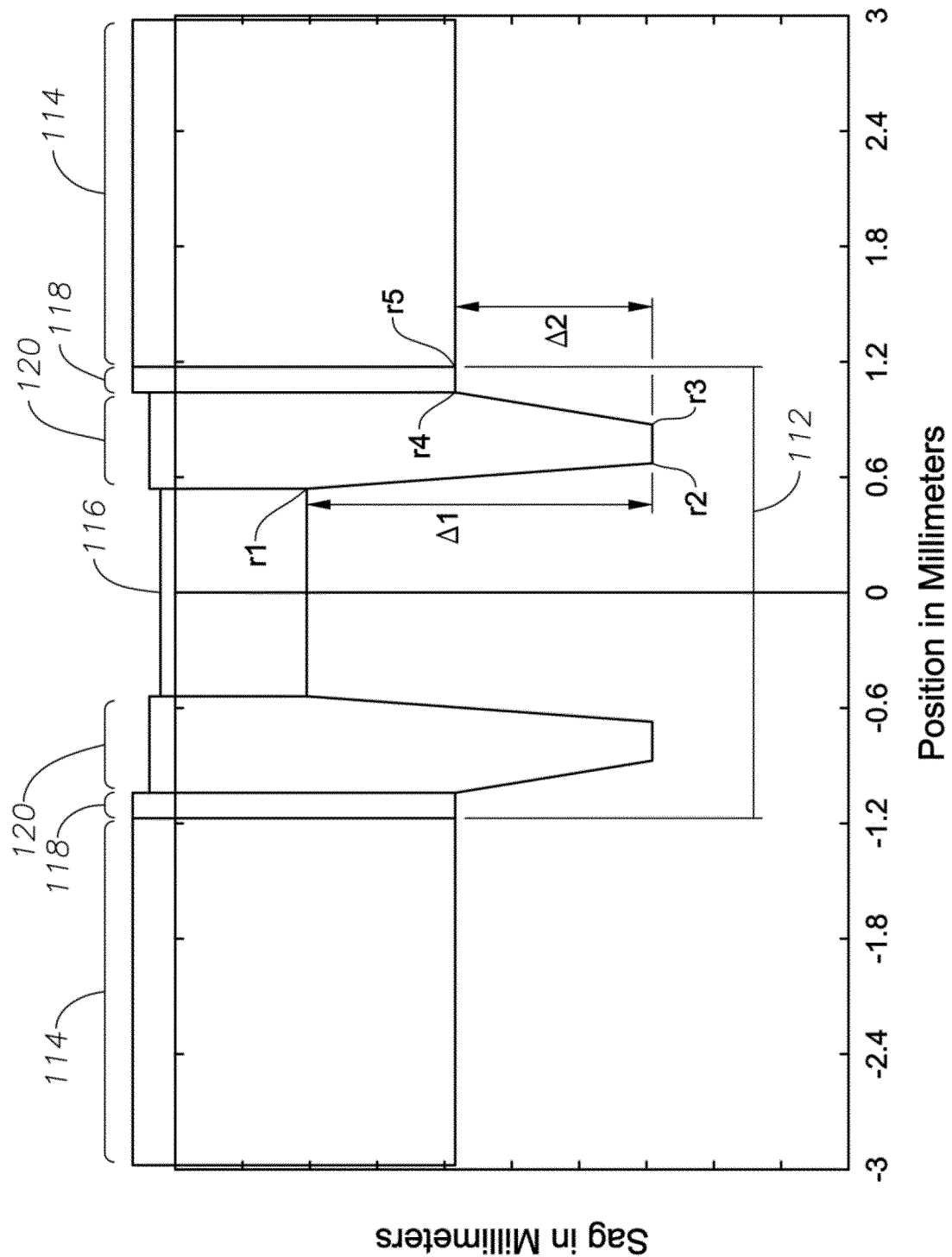

Because the first zone 112 and the second zone 114 have different base sag profiles, $\Delta_3$ (as defined in Eq. (8)) may provide for a smooth transition between the first zone 112 and the second zone 112. For example, the first zone 112 may be modified with a different base curvature (c), conic constant (k), and/or higher order coefficients ($a_2, a_4, a_6$) as compared to second zone 114 in order to shift the through focus curve in the myopic direction as compared to the through focus curve depicted in FIG. 3. FIG. 4 illustrates a plot of surface sag versus radial distance from the optical axis for an optic 102 having a surface profile defined by Eqs. (5) through (8), according to certain embodiments of the present disclosure. The surface profile plotted in FIG. 4 assumes the following values:

TABLE 1

| | |
|---|---|
| $r_1$ (mm) | 0.55 |
| $r_2$ (mm) | 0.65 |
| $r_3$ (mm) | 0.87 |
| $r_4$ (mm) | 1.05 |
| $r_5$ (mm) | 1.11 |
| $r_6$ (mm) | 3.00 |
| $\Delta_1$ (μm) | −1.02 |
| $\Delta_2$ (μm) | 0.59 |
| c (1/mm) | 19.05 |
| k | 5.99 |
| $a_2$ (1/mm) | 0 |
| $a_4$ (1/mm$^3$) | 0 |
| $a_6$ (1/mm$^5$) | 0 |
| c' (1/mm) | 20.74 |
| k' | −43.56 |
| $a_2'$ (1/mm) | 0 |
| $a_4'$ (1/mm$^3$) | 0.00019 |
| $a_6'$ (1/mm$^5$) | −0.00002 |

The values listed in Table 1 are provided for exemplary purposes only and the present disclosure contemplates that each of the values may have a range of different values. As examples, the present disclosure contemplates that $r_1$ may fall in the range of 0.3 mm to 0.7 mm, $r_4$ may fall in the range of 0.8 mm to 1.2 mm, the distance between $r_1$ and $r_2$ may fall in the range of 0 mm to 0.2 mm, and the distance between $r_3$ and $r_4$ may fall in the range of 0 mm to 0.2 mm. As additional examples, the present disclosure contemplates that $\Delta_1$ may fall within the range of −1.5 μm and −0.5 μm and $\Delta_2$ may fall within the range of 0.3 μm and 0.9 μm.

FIG. 5 illustrates a through focus plot for the optic surface profile depicted in FIG. 4 as compared to the through focus plot for the optic depicted in FIG. 2, according to certain embodiments of the present disclosure. As discussed above, modifying the first zone 112 with a different base curvature, conic constant, and/or higher order coefficients (1) rebalances the energy between intermediate and distance correction, and (2) shifts the through focus curve in the myopic direction (near target direction) as compared to the through focus curve for an optic in which the first zone 112 and the second zone 114 have the same base curvature.

A variety of techniques and materials can be employed to fabricate the above-described IOLs 100. For example, the optic 102 of an IOL 100 can be formed of a variety of biocompatible polymeric materials. Some suitable biocompatible materials include, without limitation, soft acrylic polymers, hydrogel, polymethymethacrylate, polysulfone, polystyrene, cellulose, acetate butyrate, or other biocompatible materials. By way of example, in one embodiment, the optic 102 may be formed of a soft acrylic polymer (cross-linked copolymer of 2-phenylethyl acrylate and 2-phenylethyl methacrylate) commonly known as Acrysof. The haptics 104 of the IOLs 100 can also be formed of suitable biocompatible materials, such as those discussed above. While in some cases, the optic 102 and haptics 104 of an IOL can be fabricated as an integral unit, in other cases they can be formed separately and joined together utilizing techniques known in the art.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by the following claims.

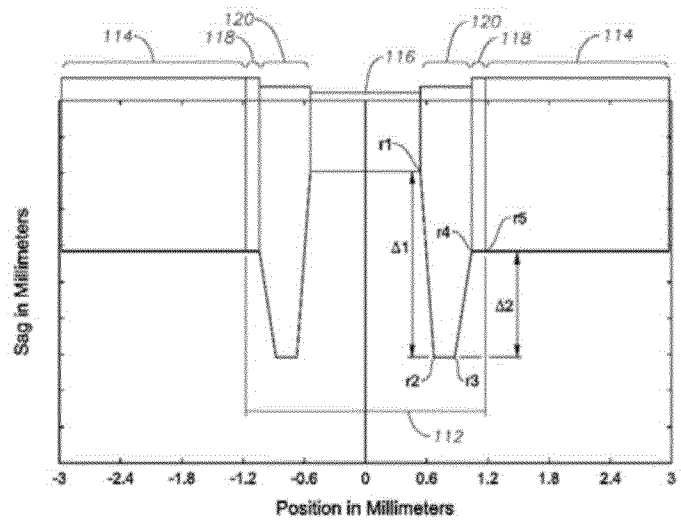

The invention claimed is:

1. An ophthalmic lens, comprising
an optic comprising an anterior surface, a posterior surface, and an optical axis, at least one of the anterior surface and the posterior surface comprising:
  a first zone extending from the optical axis to a first radial boundary; and
  a second zone extending from the first radial boundary to the edge of the optic;
wherein:
  the first zone comprises an inner region having a first curvature and an outer region having the first curvature;
  a phase shift feature separating the inner region and the outer region, the phase shift feature comprising a ridge of increased thickness relative to adjacent portions of the inner region and the outer region, the ridge comprising a ridge surface having the first curvature, a first phase shift step extending outwardly from the inner region to the ridge surface, and a second phase shift step extending inwardly from the ridge surface to the outer region.

2. The ophthalmic lens of claim 1, wherein the inner region and the outer region have the same optical power.

3. The ophthalmic lens of claim 1, wherein:
the first curvature comprises a first aspheric profile;
the second zone has a second curvature comprising a second aspheric profile, the second aspheric profile being different than the first aspheric profile.

4. The ophthalmic lens of claim 1, wherein a surface profile of the first zone is defined as follows:

$$Z_{first\ zone} = Z_{base} + Z_{2ps}$$

wherein:

$$Z_{base} = \frac{cr^2}{1 + \sqrt{1 - (1+k)c^2 r^2}} + a_2 r^2 + a_4 r^4 + a_6 r^6$$

r is a radial distance from the optical axis;
c is a base curvature of the first zone;
k is a conic constant; and
$a_2$, $a_4$, and $a_6$ are, respectively, second, fourth, and sixth order coefficients; and wherein:

$$Z_{2ps} = \begin{cases} 0 & r_0 \leq r < r_1 \\ (r - r_1)/(r_2 - r_1) * \Delta_1 & r_1 \leq r < r_2 \\ \Delta_1 & r_2 \leq r < r_3 \\ \Delta_1 + (r - r_3)/(r_4 - r_3) * \Delta_2 & r_3 \leq r < r_4 \\ \Delta_1 + \Delta_2 & r_4 \leq r < r_5 \end{cases}$$

r is a radial distance from the optical axis;
$r_0$ is the optical axis;
the inner region extends from the optical axis to $r_1$
the phase shift feature extends from $r_1$ to $r_4$;
the outer region extends from $r_4$ to $r_5$;
$\Delta_1$ is a step height of the phase shift feature relative to the inner region; and
$\Delta_2$ is a step height of the phase shift feature relative to the outer region.

5. The ophthalmic lens of claim 4, wherein a surface profile of the second zone is defined as follows:

$$Z_{second\ zone} = Z_{base} + (\Delta_1 + \Delta_2)$$

6. The ophthalmic lens of claim 1, wherein a surface profile of the optic is defined as follows:

$$Z_{optic} = Z_{base} + Z_{2ps}$$

wherein:

$$Z_{base} = \begin{cases} \dfrac{cr^2}{1+\sqrt{1-(1+k)c^2r^2}} + a_2 r^2 + a_4 r^4 + a_6 r^6 & r_0 \leq r < r_5 \\ \dfrac{c'r^2}{1+\sqrt{1-(1+k')c'^2 r^2}} + a_2' r^2 + a_4' r^4 + a_6' r^6 & r_5 \leq r < r_6 \end{cases};$$

$$Z_{2ps} = \begin{cases} 0 & 0 \leq r < r_1 \\ (r-r_1)/(r_2-r_1)*\Delta_1 & r_1 \leq r < r_2 \\ \Delta_1 & r_2 \leq r < r_3 \\ \Delta_1 + (r-r_3)/(r_4-r_3)*\Delta_2 & r_3 \leq r < r_4 \\ \Delta_1 + \Delta_2 & r_4 \leq r < r_5 \\ \Delta_3 & r_5 \leq r < r_6 \end{cases};$$

r is a radial distance from the optical axis;
$r_0$ is the optical axis;
the first zone extends from optical axis to $r_5$, with the inner region extending from the optical axis to $r_1$, the phase shift feature extending from $r_1$ to $r_4$, and the outer region extending from $r_4$ to $r_5$;
the second zone extends from $r_5$ to $r_6$;
c is a base curvature of the first zone;
k is a conic constant of the first zone; and
$a_2$, $a_4$, and $a_6$ are, respectively, second, fourth, and sixth order coefficients of the first zone;
c' is a base curvature of the second zone;
k' is a conic constant of the second zone; and
$a_2'$, $a_4'$, and $a_6'$ are, respectively, second, fourth, and sixth order coefficients of the second zone;
$\Delta_1$ is a step height of the phase shift feature relative to the inner region; and
$\Delta_2$ is a step height of the phase shift feature relative to the outer region; and $$\Delta_3 = \left[\dfrac{(cr_5^2)}{\left(1+\sqrt{(1-(1+k)c^2 r_5^2)}\right)} + a_4 r_5^4 + a_6 r_5^6 + \Delta_1 + \Delta_2\right] - \left[\dfrac{(c' r_5^2)}{\left(1+\sqrt{(1-(1+k')c'^2 r_5^2)}\right)} + a_4' r_5^4 + a_6' r_5^6\right].$$

7. The ophthalmic lens of claim 6, wherein:
at least one of the following $c \neq c'$, $k \neq k'$, $a_2 \neq a_2'$, $a_4 \neq a_4'$, and $a_6 \neq a_6'$ is true; and
$\Delta_3$ is a constant added to the base curvature of the second zone to ensure continuity between the first zone and the second zone.

8. The ophthalmic lens of claim 1, wherein a step height of the first phase shift step is greater than a step height of the second phase shift step.

* * * * *

UNITED STATES PATENT AND TRADEMARK OFFICE
CERTIFICATE OF CORRECTION

PATENT NO. : 9,968,440 B2  
APPLICATION NO. : 15/055993  
DATED : May 15, 2018  
INVENTOR(S) : Xin Hong, Zoran Milanovic and Xin Wei Page 1 of 3

It is certified that error appears in the above-identified patent and that said Letters Patent is hereby corrected as shown below:

On the Title Page

Delete the title page and substitute therefore with the attached title page consisting of the corrected illustrative figure.

In the Drawings

Please replace Fig. 2 with Fig. 2 as shown on the attached page.

Signed and Sealed this  
Seventeenth Day of March, 2020

Andrei Iancu  
*Director of the United States Patent and Trademark Office*

(12) United States Patent
Hong et al.

(10) Patent No.: US 9,968,440 B2
(45) Date of Patent: May 15, 2018

(54) OPHTHALMIC LENS HAVING AN EXTENDED DEPTH OF FOCUS

(71) Applicant: NOVARTIS AG, Basel (CH)

(72) Inventors: Xin Hong, Fort Worth, TX (US); Zoran Milanovic, Fort Worth, TX (US); Xin Wei, Frisco, TX (US)

(73) Assignee: Novartis AG, Basel (CH)

(*) Notice: Subject to any disclaimer, the term of this patent is extended or adjusted under 35 U.S.C. 154(b) by 0 days. days.

(21) Appl. No.: 15/055,993

(22) Filed: Feb. 29, 2016

(65) Prior Publication Data
US 2017/0245983 A1    Aug. 31, 2017

(51) Int. Cl.
*A61F 2/16* (2006.01)
*G02B 27/00* (2006.01)
*G02C 7/04* (2006.01)
*G02C 7/06* (2006.01)

(52) U.S. Cl.
CPC ............ *A61F 2/1618* (2013.01); *A61F 2/164* (2015.04); *A61F 2/1613* (2013.01); *A61F 2/1616* (2013.01); *A61F 2002/1683* (2013.01); *G02B 27/0075* (2013.01); *G02C 7/044* (2013.01); *G02C 7/06* (2013.01)

(58) Field of Classification Search
CPC .... A61F 2/1613; A61F 2/1616; A61F 2/1637; A61F 2/164; A61F 2/1654; A61F 2/1618; G02C 7/044; G02C 7/06
See application file for complete search history.

(56) References Cited

U.S. PATENT DOCUMENTS

| | | | |
|---|---|---|---|
| 6,536,898 B1 | 3/2003 | Cathey, Jr. | |
| 6,830,332 B2 * | 12/2004 | Piers | G02B 5/1895 351/159.11 |
| 7,025,454 B2 | 4/2006 | Cathey, Jr. | |
| 7,061,693 B2 | 6/2006 | Zalevsky | |
| 7,073,906 B1 | 7/2006 | Portney | |
| 7,365,917 B2 | 4/2008 | Zalevsky | |
| 7,859,769 B2 | 12/2010 | Zalevsky | |
| 8,192,022 B2 | 6/2012 | Zalevsky | |
| 8,430,508 B2 | 4/2013 | Weeber | |
| 8,926,092 B2 | 1/2015 | Weeber | |
| 9,216,080 B2 | 12/2015 | Bogaert et al. | |
| 9,329,407 B2 | 5/2016 | Cathey, Jr. et al. | |
| 2006/0034003 A1 | 2/2006 | Zalevsky | |
| 2010/0161051 A1 | 6/2010 | Hong | |

OTHER PUBLICATIONS

Weeber, H.A. et al., "Extending the range of vision using diffractive intraocular lens technology," J Cataract Refract Surg Jul. 2015; 41:2746-2754, 2015 ASCRS and ESCRS, 9 pgs.

\* cited by examiner

*Primary Examiner* — Howie Matthews

(57) ABSTRACT

In certain embodiments, an ophthalmic lens includes an optic having an anterior surface, a posterior surface, and an optical axis. At least one of the anterior surface and the posterior surface includes a first zone extending from the optical axis to a first radial boundary and a second zone extending from the first radial boundary to the edge of the optic. The first zone includes an inner region and an outer region separated by a phase shift feature, the phase shift comprising a ridge extending outwardly from the inner region and the outer region.

8 Claims, 6 Drawing Sheets